United States Patent
Huang et al.

(10) Patent No.: US 7,438,936 B2
(45) Date of Patent: Oct. 21, 2008

(54) DIETARY SUPPLEMENT AND RELATED METHOD

(75) Inventors: Ruo G. Huang, Long Beach, CA (US); Audra J. Davies, Long Beach, CA (US); Aaron W. Crawford, Los Angeles, CA (US); Edward S. Kahler, Anaheim, CA (US); Donald J. Pusateri, Hemet, CA (US); Stephen R. Missler, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 11/363,119

(22) Filed: Feb. 27, 2006

(65) Prior Publication Data

US 2006/0147563 A1 Jul. 6, 2006

Related U.S. Application Data

(63) Continuation-in-part of application No. 10/915,784, filed on Aug. 11, 2004, which is a continuation-in-part of application No. 10/360,789, filed on May 7, 2002, now Pat. No. 6,989,161, which is a continuation-in-part of application No. 09/878,377, filed on Jun. 12, 2001, now Pat. No. 6,511,675.

(60) Provisional application No. 60/210,746, filed on Jun. 12, 2000.

(51) Int. Cl.
  *A61K 36/00* (2006.01)
  *A61K 36/53* (2006.01)
  *A01K 36/31* (2006.01)

(52) U.S. Cl. ............... 424/736; 424/725; 424/745; 424/755; 424/777

(58) Field of Classification Search .......... 424/725
See application file for complete search history.

(56) References Cited

U.S. PATENT DOCUMENTS

| | | | |
|---|---|---|---|
| 4,115,552 A * | 9/1978 | Hamill et al. .............. 424/118 |
| 5,091,195 A * | 2/1992 | Havens ....................... 426/2 |
| 5,356,636 A | 10/1994 | Schneider et al. |
| 5,401,502 A | 3/1995 | Wunderlich et al. |
| 5,514,382 A | 5/1996 | Sultenfuss |
| 5,578,336 A | 11/1996 | Monte |
| 5,612,039 A | 3/1997 | Policappelli et al. |
| 5,654,011 A | 8/1997 | Jackson et al. |
| 5,686,108 A | 11/1997 | Pusateri et al. |
| 5,770,217 A | 6/1998 | Kutilek, III et al. |
| 5,807,586 A | 9/1998 | Jackson et al. |
| 5,830,887 A | 11/1998 | Kelly |
| 5,840,278 A | 11/1998 | Coleman |
| 5,882,646 A | 3/1999 | Pusateri et al. |
| 5,904,924 A | 5/1999 | Gaynor et al. |
| 5,948,443 A | 9/1999 | Riley et al. |
| 5,955,102 A | 9/1999 | Gorenbein et al. |
| 5,972,985 A | 10/1999 | Thomas et al. |
| 5,976,548 A | 11/1999 | Hsia et al. |
| 5,976,568 A | 11/1999 | Riley |
| 5,985,338 A | 11/1999 | Suh et al. |
| 6,022,901 A | 2/2000 | Goodman |
| 6,087,391 A * | 7/2000 | Weidner ..................... 514/458 |
| 6,129,924 A * | 10/2000 | Maurel et al. ............... 424/400 |
| 6,203,818 B1 | 3/2001 | Vester |
| 6,231,866 B1 | 5/2001 | Mann |
| 6,238,672 B1 * | 5/2001 | Chen ......................... 424/728 |
| 6,261,598 B1 | 7/2001 | Runge et al. |
| 6,375,993 B1 * | 4/2002 | Aviram et al. ............... 424/744 |
| 6,440,410 B1 | 8/2002 | Yegorova |
| 6,440,467 B2 | 8/2002 | Mann |
| 6,447,809 B1 * | 9/2002 | Krumhar et al. ............ 424/602 |
| 6,551,628 B1 | 4/2003 | Watson et al. |
| 6,579,544 B1 * | 6/2003 | Rosenberg et al. .......... 424/736 |
| 6,582,721 B1 * | 6/2003 | Lang ......................... 424/439 |
| 6,586,018 B1 | 7/2003 | Fasano |

(Continued)

FOREIGN PATENT DOCUMENTS

EP  0906761  10/1998

(Continued)

OTHER PUBLICATIONS

DW ACC 1997-000655, Nov. 1996, Derwent and DE, Kuehn.*

(Continued)

*Primary Examiner*—Christopher R Tate
*Assistant Examiner*—Randall Winston
(74) *Attorney, Agent, or Firm*—Warner Norcross & Judd LLP

(57) ABSTRACT

A dietary supplement including a unique combination of fruits, vegetables, herbs, and optionally vitamins, minerals and specialty ingredients. The supplement can include a fruit ingredient, a vegetable ingredient and an herbal ingredient, wherein the fruit ingredient is at least one of pomegranate and citrus bioflavonoids, wherein the vegetable ingredient is at least one of asparagus, lutein, lycopene and watercress, and wherein the herbal ingredient is at least one of basil, oregano and rosemary. The supplement can be administered to subjects to reduce risk factors in a subject, for example, by lowering homocysteine levels and/or reducing DNA damage. The supplement can increase plasma levels of at least one of vitamin B6, Vitamin B12, folate, and beta-carotene and other vitamins or substances in the subject.

8 Claims, 6 Drawing Sheets

U.S. PATENT DOCUMENTS

| | | |
|---|---|---|
| 6,638,545 B1 | 10/2003 | Rombi |
| 6,676,978 B1 | 1/2004 | Nair |
| 2001/0012525 A1 | 8/2001 | Mann |
| 2002/0044980 A1 | 4/2002 | Castelli et al. |
| 2002/0119173 A1 | 8/2002 | Lin et al. |
| 2002/0168429 A1 | 11/2002 | Mann |
| 2002/0192314 A1 | 12/2002 | Cho et al. |
| 2003/0049335 A1 | 3/2003 | Stier et al. |
| 2003/0108627 A1 | 6/2003 | Selzer et al. |
| 2003/0162297 A1 | 8/2003 | Ou et al. |
| 2003/0228384 A1 | 12/2003 | Kurk et al. |
| 2004/0076692 A1 | 4/2004 | Van Norren et al. |

FOREIGN PATENT DOCUMENTS

| | | |
|---|---|---|
| JP | 2001-086954 | 4/2001 |
| JP | 2001-095529 | 4/2001 |
| WO | WO 0045829 | 2/1999 |
| WO | WO 0064282 | 4/2000 |

OTHER PUBLICATIONS

Ebringer A, et al, Rheumatoid arthritis: proposal for the use of anti-microbial therapy in early cases, Scand J Rheumatol, 32(1):2-11 (2003) (abstract only).

Rossi, A, et al, Protective effects of anthocyanins from blackberry in a rat model of acute lung inflammation, Free Radic Res, 37(8):891-900 (Aug. 2003) (abstract only).

Roy, S, et al, Anti-angiogenic property of edible berries, Free Radic Res, 36(9):1023-31 (Sep. 2002) (abstract only).

Youdim, KA, et al, Potential role of dietary flavonoids in reducing microvascular endothelium vulnerability to oxidative and inflammatory insults, J Nutr Biochem, 13(5):282-288 (May 2002) (abstract only).

Calucci, L, et al, Effects of gamma-irradiation on the free radical and antioxidant contents in nine aromatic herbs and spices, J Agric Food Chem, 51(4):927-34 (2003) (abstract only).

Dragland, Steinar, et al, Several culinary and medicinal herbs are important sources of dietary antioxidants, J Nutr, 133(5) 1286-90 (May 2003) (abstract only).

Kris-Etherton, Penny M, et al, Bioactive compounds in foods: their role in the prevention of cardiovascular disease and cancer, Am J Med, 113 Suppl 9B 71S-88S (Dec. 30, 2002) (abstract only).

Tan, DX, et al, Significance of melatonin in antioxidative defense system: reactions and products, Biological Signals and Receptors, 9 (3-4) 137-59 (May-Aug. 2000) (abstract only).

Kahkonen, MP, et al, Antioxidant activity of plant extracts containing phenolic compounds, J Agr Food Chem, 47(10) 3954-62 (Oct. 1999) (abstract only).

Dragsted, LO, et al, Dietary levels of plant phenols and other non-nutritive components: could they prevent cancer?, European J Cancer Prev, 6(6) 522-8 (Dec. 1997) (abstract only).

Fejes, S, et al, Investigation of the in vitro antioxidant effect of Petroselinum crispum, Acta Pharm Hung, 68(3): 150-6 (1998) (abstract only).

Logia: Back to the Garden, downloaded from http://www.logia.net/products/back_to_garden.html (Jul. 20, 2004).

Foerster, SB et al, California's "5 a day—for better health!" campaign: an innovative population-based effort to effect large-scale dietary change, Am J Prev Med Mar.-Apr. 1995; 11 (2): 124-31.

Kant, AK, et al, A prospective study of diet quality and mortality in woman; JAMA Apr. 26, 2000; 283 (16): 2109-15.

Hennekens, CH, et al, Antioxidant vitamin-cardiovascular disease hypothesis is still promising, but still unproven; the need for randomized trials; Am J Clin Nutr Dec. 1995; 62 (6 Suppl): 1377S-1380S.

Parnetti, L, et al, Role of homocysteine in age-related vascular and non-vascular diseases, Aging (Milano) Aug. 1997; 9 (4): 241-57.

Brigelius-Flohe, R, et al, Vitamin E: function and metabolism; FASEB J Jul. 1999; 13 (10): 1145-55.

\* cited by examiner

DIETARY SUPPLEMENT AND RELATED METHOD

This is a continuation-in-part application of U.S. application Ser. No. 10/915,784, filed Aug. 11, 2004, which is a continuation-in-part of U.S. application Ser. No. 10/360,789, filed May 7, 2002 (now U.S. Pat. No. 6,989,161), which is a continuation-in-part application of U.S. application Ser. No. 09/878,377, filed Jun. 12, 2001 (now U.S. Pat. No. 6,511,675), which claims benefit of U.S. Provisional Application No. 60/210,746, filed Jun. 12, 2000, all of which are hereby incorporated by reference.

BACKGROUND OF THE INVENTION

The present invention relates to a composition and method for correcting a dietary deficiency, including an inadequacy of phytochemicals, vitamins and minerals.

Many people fail to practice healthy eating habits, such as consuming an adequate quantity and variety of food to meet U.S. Recommended Dietary Allowances. Only 22% of the subjects of a National Cancer Institute Study consumed the recommended daily number of dietary servings of fruits and vegetables—despite the fact that the recommended dietary intake of fruits and vegetables is well-known. For example, *The California Daily Food Guide: Dietary Guidelines for Californians*, California Department of Health Services (1990) recommends that each person consume at least five to nine servings of fruit and vegetables per day, including one serving of a vitamin A-rich deep green or dark orange fruit or vegetable, and at least one serving of a vitamin C-rich fruit or vegetable. Additionally, it is well reported that each person should consume at least 3 servings per week of vegetable protein in the form of legumes, nuts, or seeds. Some researchers suggest that a target of 400 grams (13 ounces) of fruits and vegetables is a sensible goal for the optimal quantity to be consumed daily. In terms of variety, it is recommended that persons should eat at least three different colors of fruits and vegetables daily.

The benefits of consuming a sufficient amount and variety of fruits and vegetables are many. For example, consuming fruits and vegetables has been shown to treat and prevent a variety of degenerative diseases. In a prospective cohort study of 41,837 postmenopausal women, the association of fruit and vegetable consumption with lung cancer risk was investigated. The researchers found that the risk of lung cancer was approximately halved when the consumption of fruits and vegetables increased from 24 or less servings to an excess of 48 servings per week. Similarly, the risk of lung cancer was approximately halved when the consumption of green leafy vegetables, including spinach and parsley sources, increased from 1 or fewer servings to six or more servings per week. Steinmetz, K. et al., "Vegetables, Fruit, and Lung Cancer in the Iowa Women's Health Study," *Cancer Res.* 53:536-43 (1993). Another study found that an increased intake of fresh tomatoes (a major source of lycopene) was associated with a pattern of protection for all sites of digestive tract cancer. Stahl, W. et al., "Lycopene: A Biologically Important Carotenoid for Humans?" *Arc. Biochem. Biophys.* 336:1-9 (1996).

In addition to fruits and vegetables, herbs also provide health benefits. For example, the herb, rosemary, contains antioxidants such as carnosol, which may play a preventive role in cholesterol oxidation. Likewise, the herb, basil is known for its antioxidant activity. Like fruits and vegetables, however, the dietary intake of beneficial herbs is unsatisfactory.

Further research has shown that the typical U.S. diet is lacking in phytochemicals. Phytochemicals generally refer to plant-derived compounds which, when taken daily in combination with vitamins and minerals, provide improved cardiovascular and bone health, an improved antioxidant profile, decreased free radical damage, and overall enhancement of the body's natural defense system.

The typical diet, especially the U.S. diet, includes an inadequate amount and variety of fruits, vegetables and herbs, as well as the phytochemicals and associated antioxidants present in these materials. A typical diet is similarly deficient in necessary vitamins and minerals associated with fruits and vegetables. Although conventional multivitamins can supplement western diets with needed vitamins and minerals, many of these multivitamins fail to provide phytochemicals that target free radicals in the body and thereby improve the antioxidant profile of the supplement.

SUMMARY OF THE INVENTION

The aforementioned problems are overcome in the present invention which provides a dietary supplement including a unique combination of fruits, vegetables, herbs, and optionally vitamins, minerals and specialty ingredients to correct a dietary deficiency of those materials.

The composition of the present invention provides substantial health benefits. For example, in one embodiment, it can support the health of people who consume a nutritionally deficient diet; improve antioxidant and nutrient status; replenish serum nutrient and phytochemical levels as a result of inadequate diets to levels associated with decreased risk of certain degenerative disease states; minimize free radical damage that occurs as a result of normal aging processes and exposure to environmental stresses; and/or improve the status of specific biomarkers indicative of optimal health, namely homocysteine, lipid byproducts, mineral status and glutathione peroxidase.

In a more specific embodiment, the composition of the present invention can provide $\beta$-carotene, $\alpha$-lipoic acid, selenium, and vitamins C and E, which improve the antioxidant profile of a person. Increased levels of folic acid and vitamins E target and improve cardiovascular health. Calcium, magnesium, and vitamin D targets and improves bone health. B vitamins improve energy metabolism. The compositions according to the invention can provide 100% of the U.S. Recommended Daily Intake of all vitamins and most minerals. The composition also can provide a variety of phytochemicals to produce a diverse antioxidant profile.

In an even more specific embodiment, the dietary supplement can include a combination of fruit, vegetable and herbal ingredients, wherein the fruit ingredients are selected from acerola, apple, blueberry, citrus bioflavonoids, cranberry, grape skin, plum, and pomegranate; wherein the vegetable ingredients are selected from asparagus, alfalfa, *brassica*, kale, lutein, lycopene, and watercress; and wherein the herbal ingredients are selected from basil, oregano, parsley, sage and rosemary. These ingredients can be concentrated, for example they may be extracted from raw ingredients. Optionally, the fruit ingredients, vegetable ingredients and herbal ingredients can be present in the composition in a ratio of about 3.5:1:1 by weight. Specialty ingredients, such as alpha lipoic acid and inositol can be added to the composition.

In yet another embodiment, the dietary supplement can include at least one fruit ingredient selected from the group consisting of citrus bioflavonoids and pomegranate, and optionally at least one of acerola, apple, blueberry, cranberry, grape skin, plum and raspberry; at least one vegetable ingredient selected from the group consisting of asparagus, lutein, lycopene, and watercress, and optionally at least one of alfalfa, *brassica*, and kale; and at least one herbal ingredient selected from the group consisting of basil, oregano and rosemary, and optionally at least one of parsley and sage.

According to another aspect, there is provided a method for correcting a deficiency of nutrients, vitamins and/or phytochemicals by administering a dietary supplement to a subject, the supplement including at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, *brassica*, and kale; and at least one herbal ingredient selected from the group consisting of basil, oregano and rosemary, and optionally at least one of parsley and sage.

In yet another aspect, there is provided a method for improving the antioxidant profile of the human body comprising administering an effective amount of a dietary supplement to a subject, the supplement comprising at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, *brassica*, and kale; and at least one herbal ingredient selected from the group consisting of basil, oregano and rosemary, and optionally at least one of parsley and sage.

In a fourth aspect, provided is a method for decreasing free radical damage in the human body comprising administering an effective amount of a dietary supplement including at least one fruit ingredient selected from the group consisting of citrus bioflavonoids and pomegranate, and optionally at least one of acerola, apple, blueberry, cranberry, grape skin, plum and raspberry; at least one vegetable ingredient selected from the group consisting of asparagus, lutein, lycopene, and watercress, and optionally at least one of alfalfa, *brassica*, and kale; and at least one herbal ingredient selected from the group consisting of basil, oregano and rosemary, and optionally at least one of parsley and sage.

In a fifth aspect, a method is provided for enhancing the immune system of the human body comprising administering an effective amount of a dietary supplement including at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, *brassica*, and kale; and at least one herbal ingredient selected from the group consisting of basil, oregano and rosemary, and optionally at least one of parsley and sage.

In a sixth aspect, a method is provided for reducing risk factors in the human body by administering an effective amount of a dietary supplement including at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, *brassica*, and kale; and at least one herbal ingredient selected from the group consisting of basil, oregano and rosemary, and optionally at least one of parsley and sage. Risk factors are conditions or levels of substances in a body that affect the odds that now-healthy people have of developing a given disease, such as cardiovascular disease, coronary disease, and/or occlusive vascular disease later. Exemplary reduced risk factors include, but are not limited to, lowered homocysteine levels and reduced DNA damage.

These and other objects, advantages and features of the invention will be more readily understood and appreciated by reference to the detailed description of the invention and the drawings. It is to be understood that both the foregoing general description and the following detailed description are exemplary and explanatory only and are not restrictive of the invention as claimed.

DETAILED DESCRIPTION OF THE INVENTION

I. Overview

Figure 1:
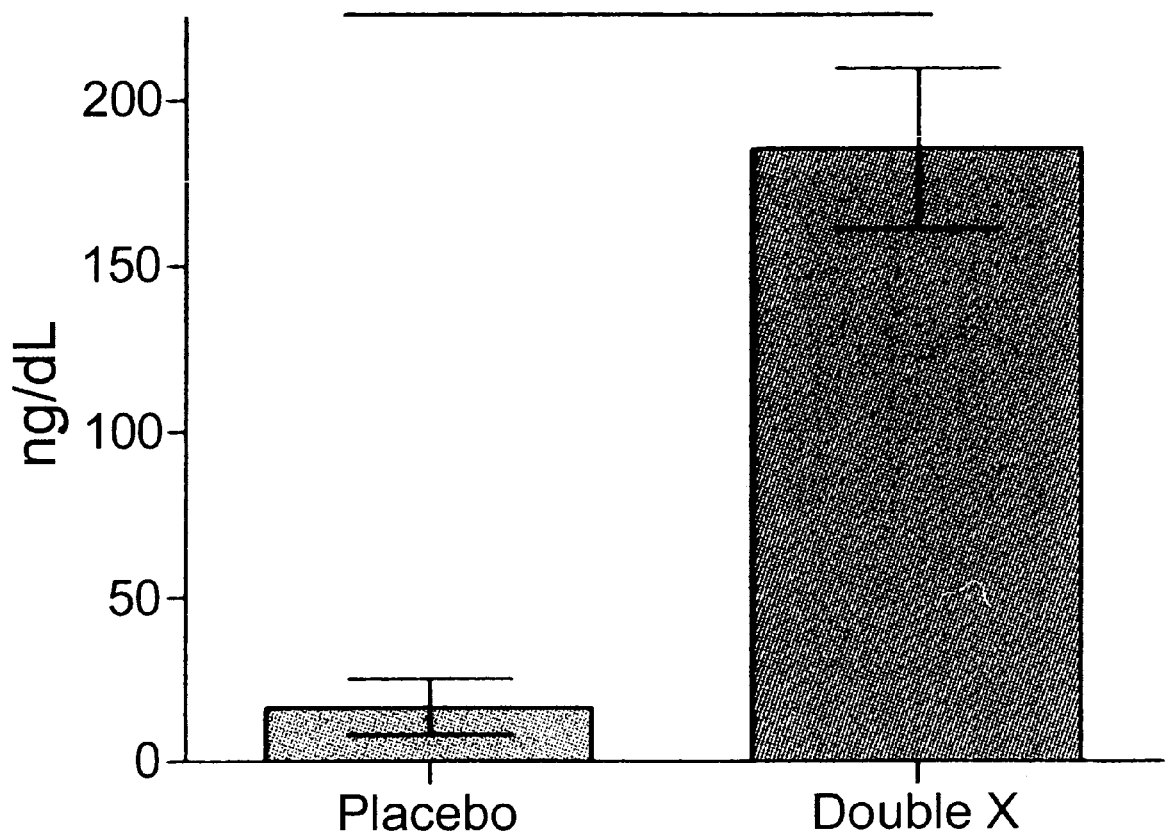
FIG. 1 is a graphical illustration of changes in vitamin levels measured in clinical testing of an embodiment of the supplement of the present invention explained in Example 3 below.

In general, the invention relates to a dietary supplement composition comprising fruits, vegetables and herbs. In one embodiment, the composition can include a fruit ingredient, a vegetable ingredient and an herbal ingredient, wherein the fruit ingredient is at least one of pomegranate and citrus bioflavonoids, wherein the vegetable ingredient is at least one of asparagus, lutein, lycopene and watercress, and wherein the herbal ingredient is at least one of basil, oregano and rosemary.

The following fruit ingredients also can be present in the dietary supplement: acerola, apple, blueberry, cranberry, grape skin, and plum. Further, the following vegetable ingredients also can be present in the dietary supplement: alfalfa, *brassica*, and kale. Finally, the following herbal ingredients also can be present in the dietary supplement: sage and parsley.

The invention also relates to a method for correcting a diet-induced deficiency of fruits, vegetables and herbs, and the nutrients present in such materials. The dietary supplement of the present invention additionally can contain phytochemicals, vitamins, and minerals known to improve the body's natural defenses against oxidants, free radicals, and diseases. Further, the dietary supplement can be used to reduce health risk factors, for example, it can be used to lower homocysteine levels and reduce DNA damage, among other things.

II. Dietary Supplement and Method of Manufacture

The dietary supplement can include a combination of fruit, vegetable, herbal and other ingredients that provide significant health benefits. The following tables illustrate representative daily amounts of suitable fruits, vegetables, herbs, vitamins, and minerals which can be included in the supplement.

The dosages can be varied as desired from application to application. For example, Dosage A represents a range of dosages of the respective ingredients that is suitable for purposes of the present invention. Dosage B represents a dosage of a particular embodiment. The unit "mg" in Tables 1-5 means that that the amount recited is given in the number of, e.g., milligrams, provided in a two-tablets per day dosage, unless otherwise noted, e.g., "IU" is recited. Thus, to determine the amount of a specific ingredient per single tablet, the amount recited in the respective tables must be halved.

TABLE 1

| Fruit Ingredient | Dosage A, mg/day | Dosage B, mg/day |
| --- | --- | --- |
| Acerola Powder | 50-500 | 300 |
| Apple extract | 25-1000 | 50 |
| Citrus Bioflavanoids | 25-1000 | 100 |
| Grape skin extract | 25-1000 | 50 |
| Plum extract | 25-1000 | 50 |
| Cranberry extract | 25-1000 | 50 |
| Pomagranate | 5-500 | 25 |
| Blueberry extract | 25-1000 | 50 |

The citrus bioflavonoids are commercially available from Access Business Group International LLC of Ada, Mich. These ingredients can be in a concentrate form, and can include naringen, hesperidin and narirutin.

TABLE 2

| Vegetable Ingredient | Dosage A, mg/day | Dosage B, mg/day |
| --- | --- | --- |
| Asparagus | 25-1000 | 50 |
| Alfalfa | 25-1000 | 70 |
| Brassica | 25-1000 | 50 |
| Kale | 20-1000 | 75 |
| Lycopene | 0.1-100 | 2 |
| Lutein esters | 0.1-100 | 2 |
| NUTRILITE Watercress | 5-500 | 28 |

NUTRILITE watercress is available from Access Business Group International LLC. The *Brassica* and/or kale can be in dehydrated, powdered form. As used herein the *Brassica* ingredient may include any material derived from plants in the Brassicae family, for example, broccoli. The lutein esters used in the supplement can be of the type sold under the name Xangold 10% beadlets, which is available from Cognis Nutrition & Health of Cincinnati, Ohio. The lycopene used in the supplement can be of the type sold under the name Lycobeads 5%, which is available from H. Reisman Corp. of Orange, N.J.

TABLE 3

| Herbal Ingredient | Dosage A, mg/day | Dosage B, mg/day |
| --- | --- | --- |
| Basil extract | 25-1000 | 50 |
| Rosemary extract | 25-1000 | 50 |
| Sage | 5-500 | 25 |
| Oregano extract | 25-1000 | 50 |
| NUTRILITE Parsley | 5-500 | 25 |

NUTRILITE parsley is available from Access Business Group International LLC. The dietary supplement can also include ingredients in addition to the fruit, vegetable and herbal ingredients noted above. For example, suitable vitamins for use in the compositions and methods of the present invention can include, vitamin A, vitamin B1, vitamin B2, vitamin B6, vitamin B12, niacin/niacinamide, pantothenic acid, folic acid, biotin, choline, vitamin C, vitamin D, and vitamin E. Table 4 below includes a suitable vitamin profile.

TABLE 4

Vitamin Profile

| Ingredient | Dosage A, mg/day | Dosage B, mg/day |
| --- | --- | --- |
| Vitamin C from Acerola Powder | 20-100 | 60 |
| Ascorbic Acid (C) | 100-700 | 440 |
| Vitamin A from Beta Carotene | 1000-10,000 IU | 7500 IU |
| Biotin | 0.01-4 | 0.300 |
| Pantothenic Acid from Cal Pan Gran | 5-300 | 50 |
| Choline | 10-400 | 50 |
| Folic Acid | 0.01-10 | 0.8 |
| Inositol | 5-100 | 25 |
| Vitamin E | 10-5000 IU | 150 IU |
| Mixed Tocopherols | 5-300 | 50 |
| Niacin/Niacinamide | 5-300 | 40 |
| Pyridoxine (B6) | 10-100 | 15 |
| Riboflavin (B2) | 1-100 | 12.75 |
| Thiamine (B1) | 1-100 | 11.25 |
| Vitamin A from Acetate | 100-10,000 IU | 2500 IU |
| Vitamin B12 | 0.01-50 | 0.045 |
| Vitamin D3 | 10-2000 IU | 400 IU |
| Yeast, Standardized@ (source of 100% RDA Bs) | 5-350 | 60 |

In addition to the vitamins listed above, minerals for use in the compositions and methods of the present invention include, for example, boron, calcium, chromium, copper, iodine, magnesium, manganese, molybdenum, potassium, selenium, vanadium, and zinc. Other vitamins and minerals may also be used. Table 5 below includes a mineral profile suitable for the supplement of the present invention.

TABLE 5

Mineral Profile

| Ingredient | Dosage A, mg/day | Dosage B, mg/day |
| --- | --- | --- |
| Calcium | 100-2000 | 750 |
| Chromium | 0.01-5 | 0.120 |
| Copper | 0.01-5 | 2 |
| Iodine | 0.001-5 | 0.15 |
| Magnesium | 10-1000 | 300 |
| Manganese | 1-20 | 5 |
| Molybdenum | 0.001-75 | 0.075 |
| Potassium | 5-300 | 80 |
| Selenium | 0.001-5 | 0.100 |
| Zinc | 1-50 | 15 |

With the ingredients of Tables 1-3, and optionally the ingredients of Tables 4-5, the dietary supplement of the present invention can provide a significant portion of, and in many cases exceed, the recommended daily requirement for a variety of vitamins and minerals. Tables 6 and 7 below illustrate the potency of the dietary supplement, when taken in the above daily amounts, in terms of percentages of the daily requirements for the listed vitamins and minerals.

TABLE 6

| Vitamin | Amount/Day | % Daily Value |
| --- | --- | --- |
| Vitamin A (75% as β-Carotene), IU | 10,000 | 200% |
| Vitamin C, mg | 500 | 833% |
| Vitamin D, IU | 400 | 100% |

TABLE 6-continued

| Vitamin | Amount/Day | % Daily Value |
|---|---|---|
| Vitamin E, IU | 150 | 500% |
| Niacin/Niacinamide, mg | 40 | 200% |
| Vitamin $B_6$, mg | 15 | 750% |
| Vitamin $B_{12}$, mcg | 45 | 750% |
| Folic Acid, mcg | 800 | 200% |
| Biotin, mcg | 300 | 100% |
| Pantothenic Acid, mg | 50 | 500% |

TABLE 7

| Minerals | Amount/Day | % Daily Value |
|---|---|---|
| Calcium, mg | 750 | 75% |
| Magnesium, mg | 300 | 75% |
| Iodine, mcg | 150 | 100% |
| Potassium, mg | 80 | 2% |
| Copper, mg | 2 | 100% |
| Zinc, mg | 15 | 100% |
| Manganese, mg | 5 | 100% |
| Chromium, mcg | 120 | 100% |
| Selenium, mcg | 100 | 143% |
| Molybdenum, mcg | 75 | 100% |

Additional specialty ingredients which can be used in the dietary supplement include, for example, methyl sulfonyl methane (MSM), α-lipoic acid (10 mg/day), catechins, polyphenols, flavanoids, lycopene, lutein, yeast, inositol, and para-aminobenzoic acid (PABA).

The dietary supplement of the present invention can be formulated using any pharmaceutically acceptable form of respective fruit concentrates, vegetable concentrates, herb concentrates, phytochemicals, vitamins, minerals, and other nutrients, including their salts. The supplements can be formulated into tablets, powders, gels, or liquids (a tablet, for the purposes of the present invention and as used throughout the application disclosure, refers to any form of a solid oral dosage, including but not limited to tablets, caplets, capsules, powders, etc.). The dietary supplements can be formulated as powders, for example, for mixing with consumable liquids such as milk, juice, water, or consumable gels or syrups for mixing into other dietary liquids or foods. The dietary supplements can also be formulated with other foods or liquids to provide pre-measured supplemental foods, for example, single-serving bars. Flavorings, binders, protein, complex carbohydrates, and the like can be added as needed.

According to one aspect of the invention, the dietary supplement is administered as three separate tablets, all three of which are administered twice a day; however, the dietary supplement may be administered in other forms and unit dosages as desired.

The dietary supplement of the present invention will be illustrated by, but is not intended to be limited to, the following examples.

EXAMPLE 1

Three tablets may be prepared to provide a) fruit, vegetable and herbal ingredients, b) vitamins and c) minerals. The first tablet includes the fruit, vegetable and herbal ingredients of Tables 1-3. The amount of each ingredient in this first tablet is half of the amount listed in the Dosage B of the Tables, as the table-listed amount is the amount present in two such tablets. The first tablet may also include carriers and other tableting aids such as silicon dioxide, magnesium oxide, calcium carbonate, croscarmellose sodium, microcrystalline cellulose and magnesium stearate in amounts that may be varied for purposes well known to those of skill in the art.

The second tablet includes vitamins of Table 4. The amount of each ingredient in this second tablet is half of the amount listed in the Table, as the table-listed amount is the amount present in two such tablets. The second tablet may also include carriers and other tableting aids such as microcrystalline cellulose, calcium carbonate, croscarmellose sodium, magnesium stearate, and silicon dioxide.

The third tablet includes minerals of Table 5. The amount of each ingredient in this third tablet is half of the amount listed in the Table, as the table-listed amount is the amount present in two such tablets. The third tablet may also include carriers and other tableting aids such as microcrystalline cellulose, calcium carbonate, croscarmellose sodium, magnesium stearate, and silicon dioxide.

The three tablets, when administered twice a day, complete the gap in phytochemicals that is present in the typical diet.

EXAMPLE 2

The following examples relate to methods of preparing the above three tablets. The ingredients are the same as those referred to above in Tables 1-5. For purposes of the following examples, however, tablets including the fruit, vegetable and herbal ingredients from Tables 1-3 are referred to as "Tablet 1"; tablets including the vitamin ingredients from Table 4 are referred to as "Tablet 2"; and tablets including the mineral ingredients from Table 5 are referred to as "Tablet 3." It is noted that other methods for preparing the tablets and other suitable delivery vehicles can be used as desired.

Tablet 1

Mixed tocopherols, D-alpha-tocopherol (succinate), and silicon dioxide (NF fine powder) are passed through a SWECO separator equipped with a 20 mesh screen into a 100 cubic foot PK blender. The ingredients are blended for ten minutes. Magnesium oxide (D.C. heavy), Acerola concentrate, citrus bioflavonoids complex, plum extract, apple extract, rosemary extract, basil extract, grape skin extract, cranberry extract, kale powder, asparagus extract, blueberry extract, parsley dehydrate, oregano extract, sage extract, pomegranate extract, and inositol are passed through a SWECO separator equipped with a 20 mesh screen into a 100 cubic foot PK blender. The ingredients are blended for ten minutes.

Lycopene (5%), lutein ester (beadlets), mixed tocopherols, calcium carbonate (granular), croscarmellose sodium and microcrystalline cellulose (silicified) are passed through a SWECO separator equipped with a 20 mesh screen directly into a 100 cubic foot PK blender. The mixture is blended for ten minutes. Next, magnesium stearate (Kosher) is passed through a SWECO separator equipped with a 20 mesh screen directly into a 100 cubic foot PK blender. The ingredients are blended for an additional five minutes. The resulting mixture is discharged into totes or supersacks, and compressed into tablets.

Tablet 2

Acerola concentrate, microcrystalline cellulose (silicified) and alpha lipoic acid are passed through a SWECO separator equipped with a 20 mesh screen directly into a 100 cubic foot P.K. blender. The ingredients are blended for ten minutes. Next, the following ingredients are passed through a SWECO separator equipped with a 20 mesh screen directly into the 100 cubic foot PK blender: thiamine mononitrate (97%), riboflavin, niacinamide, biotin trituration (1%), vitamin B12 (1.1%), calcium pantothenate granular, folic acid, pyridoxine HCl (95%), and choline bitartrate. The ingredients are blended for ten minutes. Next, the following items are passed through a SWECO separator equipped with a 20 mesh screen directly into the 100 cubic foot PK blender: beta carotene (beadlets), vitamin D3 (beadlets), yeast (standardized) and vitamin A (acetate). The mixture is blended for an additional ten minutes.

Next, the following ingredients are passed through a SWECO separator equipped with a 20 mesh screen directly into the 100 cubic foot PK blender: ascorbic acid (97%), calcium carbonate (granular), croscarmellose sodium, d-alpha-tocopherol succinate, silicon dioxide (NF fine powder). The mixture is blended for an additional ten minutes.

Next, magnesium stearate (Kosher) is passed through a SWECO separator equipped with a 20 mesh screen directly into the 100 cubic foot PK blender. The mixture is blended for an additional five minutes. The resulting mixture is discharged into totes or supersacks, and compressed into tablets.

Tablet 3

Zinc amino acid chelate, mixed tocopherols and silicon dioxide (NF fine powder) are passed through a SWECO separator equipped with a 20 mesh screen into a 100 cubic foot PK blender. The ingredients are blended for ten minutes. Co-processed alfalfa concentrate/microcrystalline cellulose/calcium carbonate, selenium yeast, microcrystalline cellulose, copper amino acid chelate, manganese amino acid chelate, potassium iodide trituration, chromium amino acid chelate, molybdenum amino acid chelate, *brassica* dehydrate, watercress dehydrate and croscarmellose sodium are passed through a SWECO separator equipped with a 20 mesh screen directly into a 100 cubic foot PK blender. The ingredients are blended for ten minutes.

Potassium chloride, magnesium oxide (D.C. heavy) and calcium carbonate (granulation) are passed through a SWECO separator equipped with a 20 mesh screen directly into a 100 cubic foot PK blender. The ingredients are blended for ten minutes. Next, magnesium stearate (Kosher) is passed through a SWECO separator equipped with a 20 mesh screen directly into a 100 cubic foot PK blender. The ingredients are blended for an additional ten minutes. Next, magnesium stearate (Kosher) is passed through a SWECO separator equipped with a 20 mesh screen directly into the 100 cubic foot PK blender. The mixture is blended for an additional five minutes. The resulting mixture is discharged into totes or supersacks, and compressed into tablets.

EXAMPLE 3

A study was conducted to confirm the efficacy of the supplement of the present invention on multiple levels; first, by analyzing whether the supplement affected the risk factors for disease, such as cardiovascular disease, coronary disease, and/or occlusive vascular disease, in the test subjects (risk factors are conditions or levels of substances in a body that affect the odds that now-healthy people have of developing a given disease). Second, by analyzing the levels in the bloodstream of the health promoting ingredients of the supplement.

Based on the testing, it was determined that consumption of the supplement addressed at least two risk factors: it reduced homocysteine levels, and it reduced DNA damage. In addition, consumption of the supplement corrected dietary deficiencies of phytochemicals; improved the amount of antioxidants in the body; decreased free radical damage; increased plasma vitamin, mineral and phytochemical concentrations; and improved plasma and systemic antioxidant capacity, among other things.

Homocysteine monitoring was chosen because it is a by-product of protein metabolism via methionine. Moreover, homocysteine is known to induce DNA strand breakage, oxidative stress and apoptosis (cell death). Insufficient recycling of homocysteine into cysteine by vitamin B6 or back into methionine by folic acid and B6 leads to elevated plasma homocysteine levels and increased risk for age-related health issues. DNA stability/damage monitoring was also chosen because it is believed that this is a sensitive early marker of risk of chronic health conditions.

The subjects in the study were healthy men and women, from 18 to 80 years of age, who consume fewer than 12 items found on the Recommended Foods Checklist per week. These subjects were selected after administration of a food frequency questionnaire and application of the Recommended Foods Score (RFS). The RFS consists of 23 foods, 14 of which are fruits and vegetables, that when consumed on a weekly basis have been associated with reduced mortality. This was demonstrated in a cohort study of 42,254 women. Those with a mean RFS of 16.0 (highest quartile) had an all-cause mortality relative risk of 0.69 compared to those with a mean RFS of 6.4 (lowest quartile). It was noted that those in the highest quartile consumed significantly more calories (131%), fiber (200%), Vitamin C (230%), folate (181%), and pro-Vitamin A carotenoids (253%) compared to those in the lowest quartile.

The clinical study encompassed a double-blind (that is, to subjects and to investigators) study of 120 subjects over a six-week period. During the six-week trial, subjects consumed three tablets of study product, twice a day with morning and evening meals. The product consumed was either a labeled dose of Double X 2005 or a placebo. In one test, the Double X 2005 product included at least one fruit ingredient selected from the group consisting of citrus bioflavonoids (100 mg/day) and pomegranate (25 mg/day), and optionally at least one of acerola (as source of 500 mg Vitamin C), apple (50 mg/day), blueberry (50 mg/day), cranberry (50 mg/day), grape skin (50 mg/day), and prune extract (50 mg/day); at least one vegetable ingredient selected from the group consisting of asparagus (50 mg/day), lutein (2mg/day), lycopene (2 mg/day), and watercress (28 mg/day), and optionally at least one of alfalfa (70 mg/day), *brassica* (48 mg/day), and kale (75mg/day); and at least one herbal ingredient selected from the group consisting of basil (50 mg/day), oregano (50 mg/day) and rosemary (50 mg/day), and optionally at least one of parsley (25 mg/day) and sage (25 mg/day).

The subjects were tested by taking blood and urine samples and performing the following assays: total polyphenols, plasma ORAC (Oxygen Radical Absorption Capacity), CP450 enzyme induction, cytokinesis block assay, comet assay, bioenergetics assay, urinary bile acids, B6, B12, folate, Vitamin C, homocysteine, alpha and gama tocopherols, beta-carotene, C-reactive protein and urinary 8-epi prostaglandins F2α, which were tested at baseline, two weeks, four weeks and six weeks into the study. These assays are generally well known, and will not be described in detail here. Improvement, and thus, efficacy of the supplement, was measured based on: plasma concentrations of vitamins, minerals and phytochemicals; homocysteine levels; DNA stability; plasma and systemic antioxidant capacity; detoxification capacity; cellular energy dynamics; genomic stability; other risk factors and subjective effects.

Figure 2:
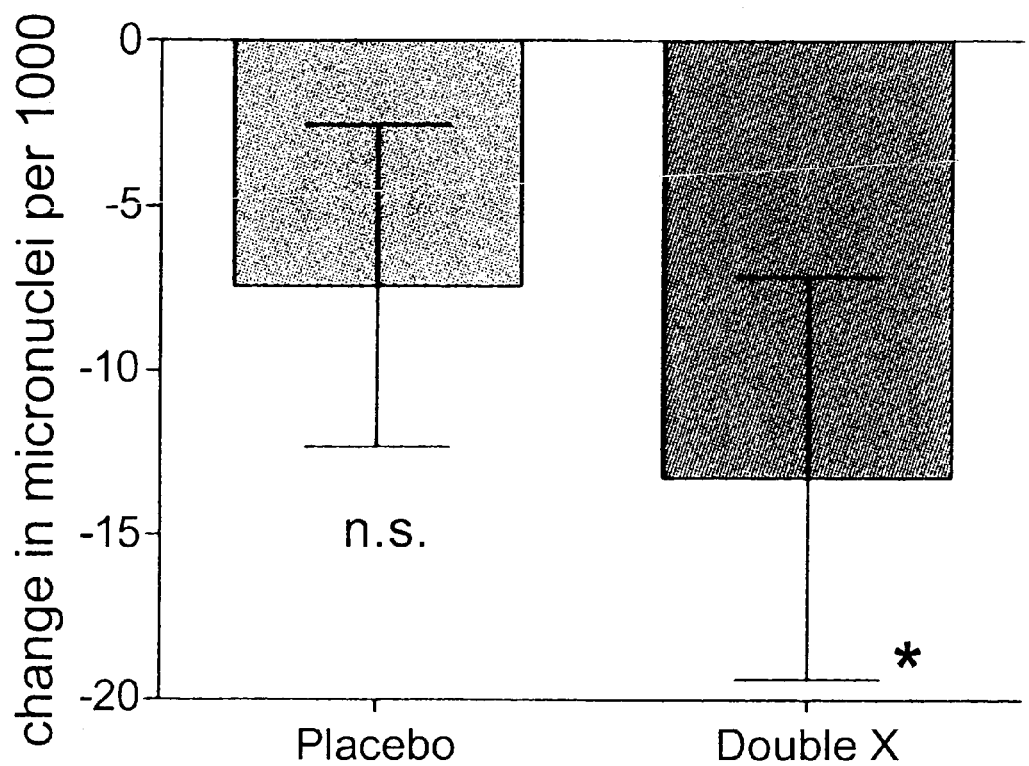
FIG. 2 is a graphical illustration of changes in micronuclei count measured in the clinical testing.
Figure 3:
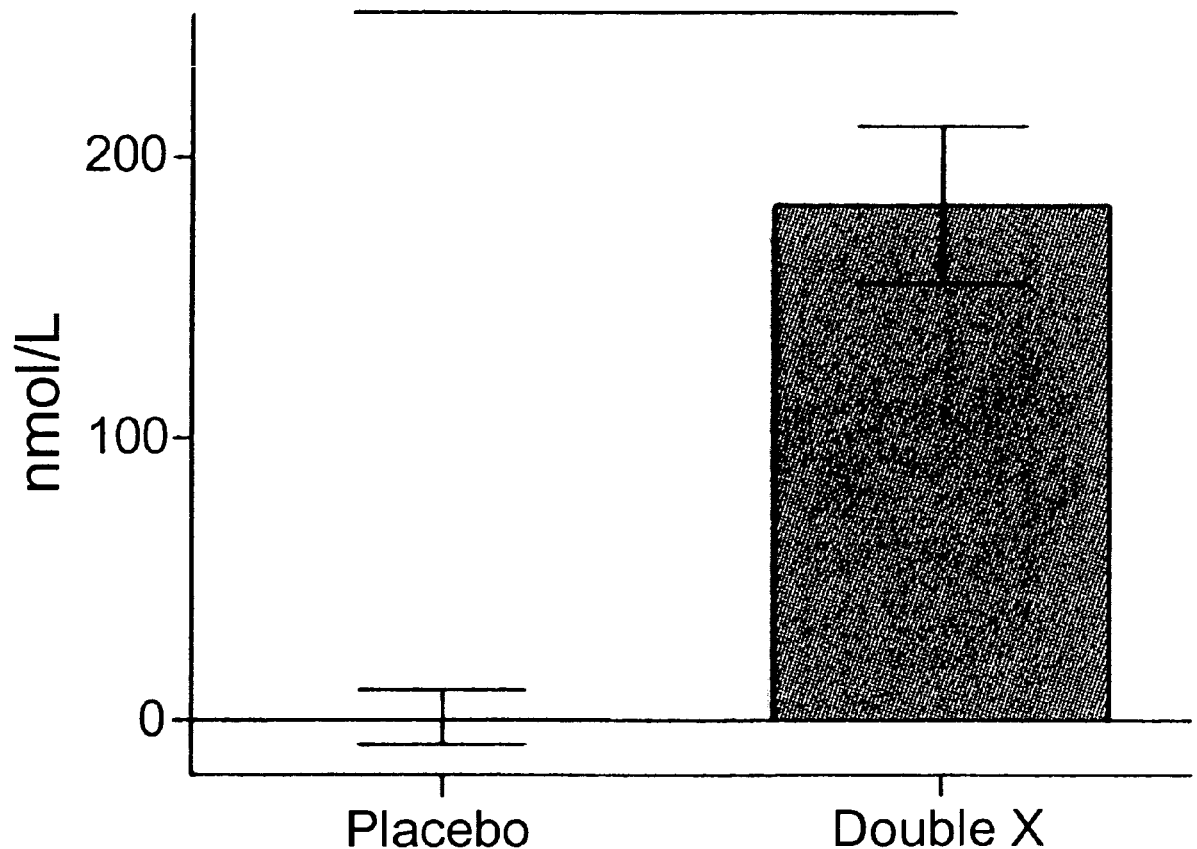
FIG. 3 is a graphical illustration of changes in vitamin levels measured in the clinical testing.
Figure 4:
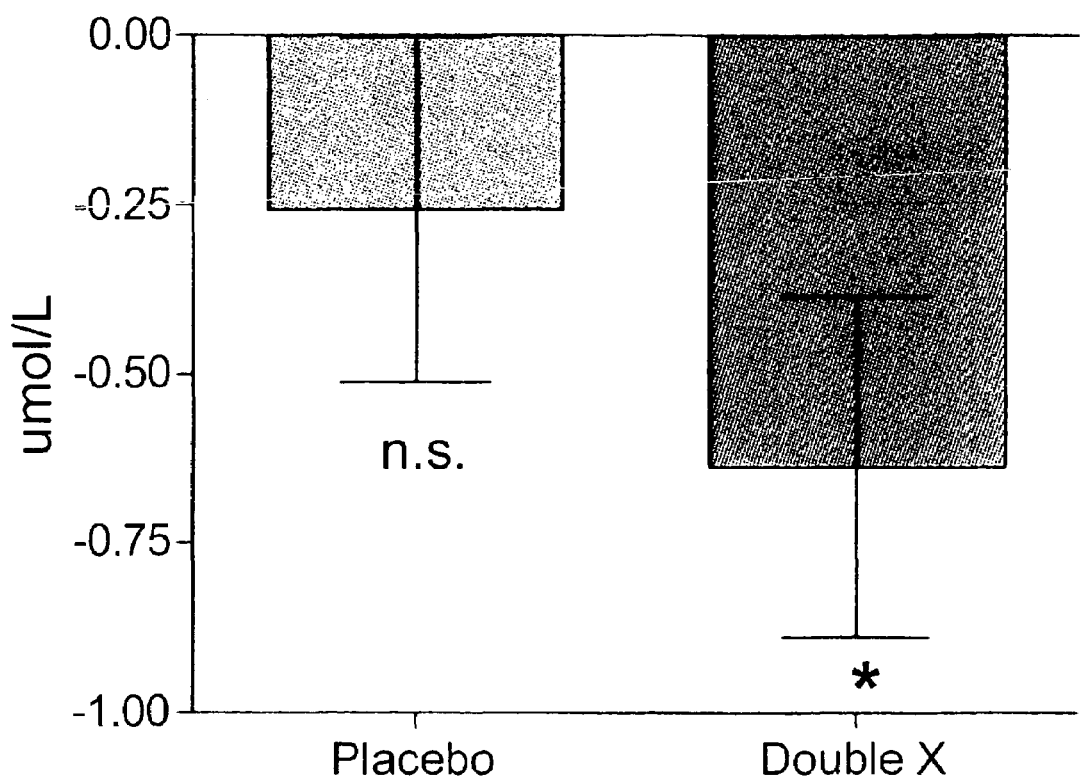
FIG. 4 is a graphical illustration of changes in homocysteine levels measured in the clinical testing.
Figure 5:
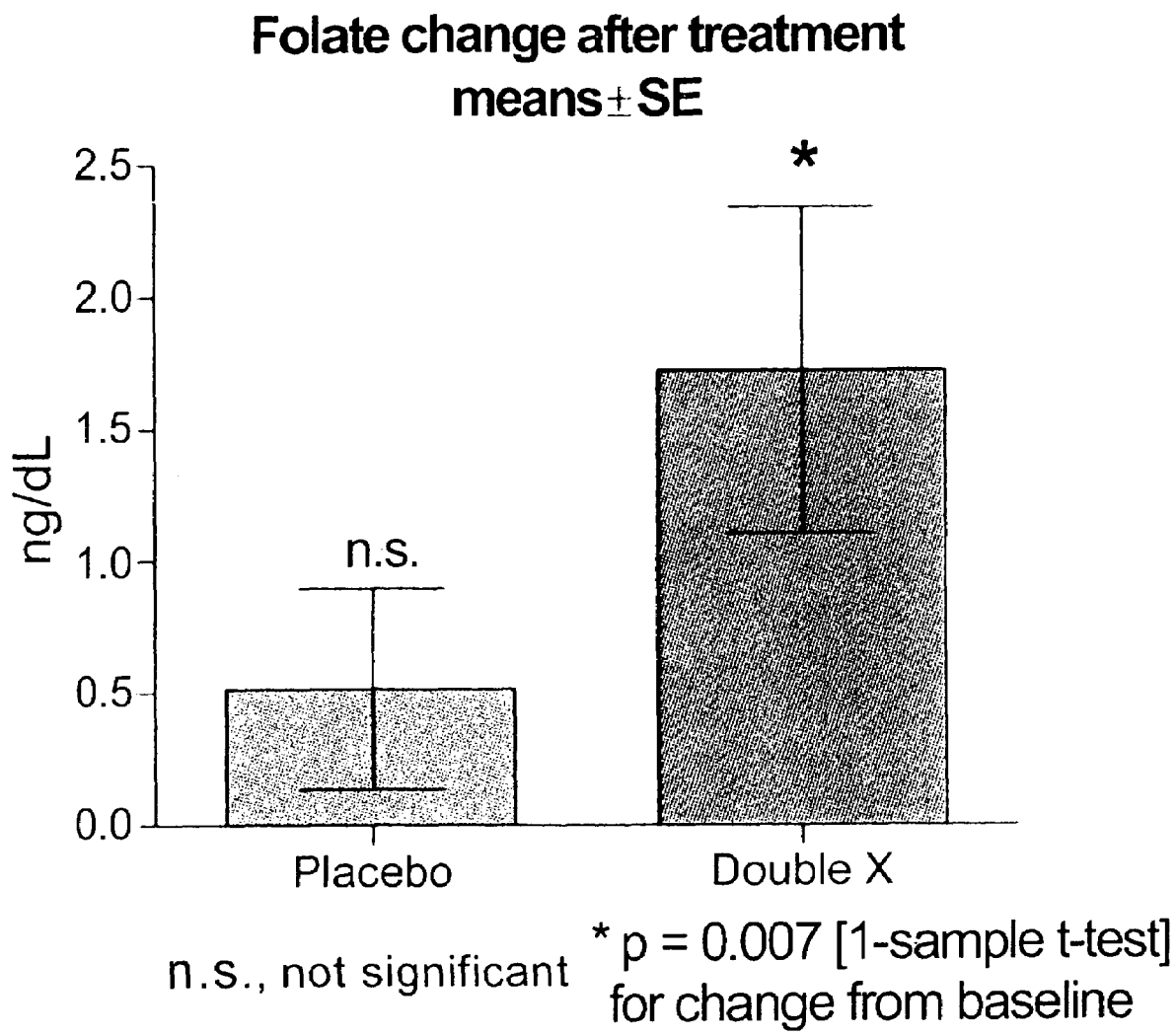
FIG. 5 is a graphical illustration of changes in folate levels measured in the clinical testing.
Figure 6:
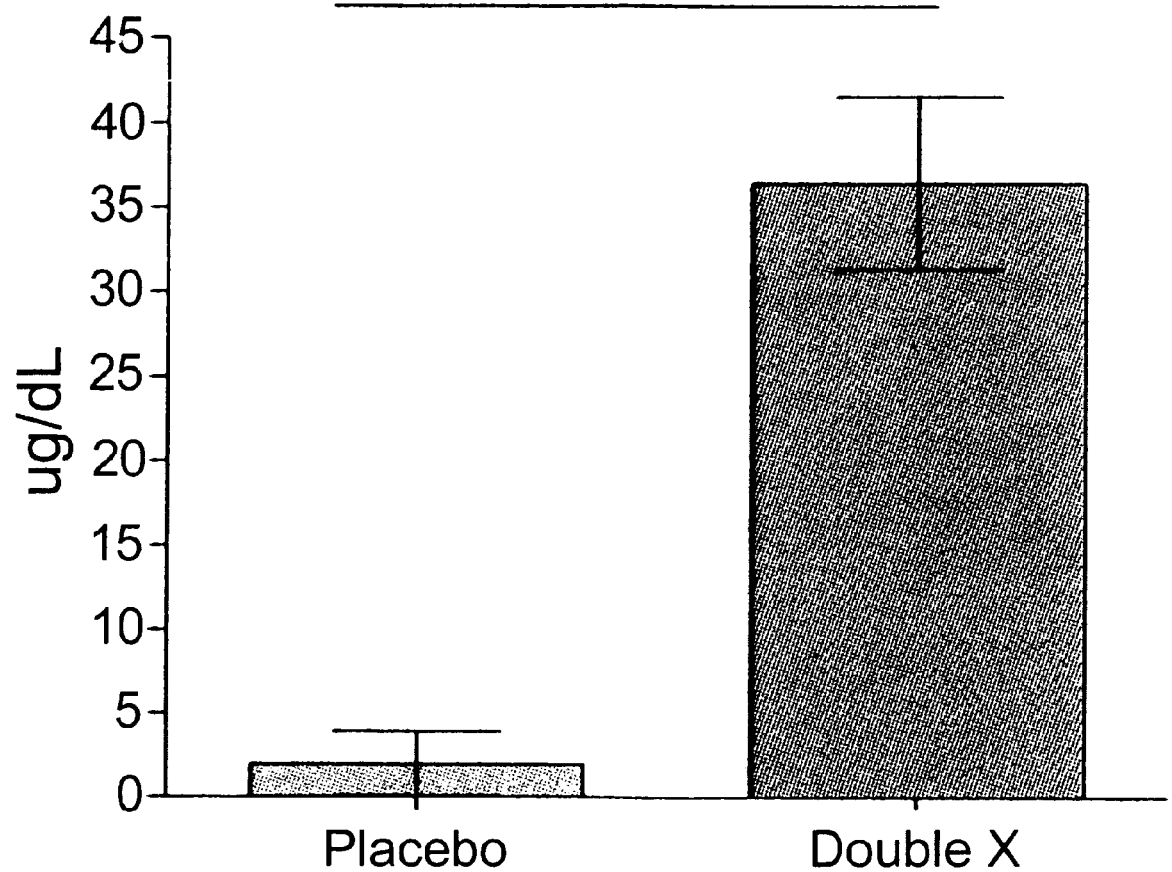
FIG. 6 is a graphical illustration of changes in beta carotene levels measured in the clinical testing.

Of the 120 subjects randomized at the start of the study, 118 completed the study. Due to sample stability issues, analyzable samples ranged from 90 to 100, depending on the assay. Table 8 below lists pre-treatment (baseline) and post-treatment (that is, after taking Double X or placebo for six weeks) blood test results for the listed outcome measures. FIGS. 1-6 graphically illustrate the changes in outcome measures for B12, micronuclei, B6, homocysteine, folate, and beta-carotene.

TABLE 8

| Measure | Placebo pre-treatment | | | Placebo post-treatment | | | Double X pre-treatment | | | Double X post-treatment | | |
|---|---|---|---|---|---|---|---|---|---|---|---|---|
| | Mean | SD | n | Mean | SD | n | Mean | SD | n | Mean | SD | n |
| Beta-Carotene μg/dL | 24.10 | 23.42 | 50 | 26.07 | 24.30 | 50 | 30.43 | 25.05 | 50 | 66.85 | 52.12 | 50 |
| Alpha-Tocopherol mg/L | 9.11 | 4.98 | 51 | 9.21 | 3.53 | 51 | 9.17 | 4.16 | 50 | 11.58 | 4.02 | 50 |
| Gamma-Tocopherol mg/L | 1.84 | 0.89 | 51 | 2.20 | 1.31 | 51 | 1.78 | 1.37 | 50 | 1.53 | 0.74 | 50 |
| vitamin C mg/dL | 0.92 | 0.86 | 21 | 0.95 | 0.87 | 21 | 0.74 | 0.51 | 26 | 0.99 | 0.49 | 26 |
| Folate ng/dL | 9.57 | 3.34 | 49 | 10.08 | 3.96 | 49 | 10.95 | 3.78 | 50 | 12.67 | 3.72 | 50 |
| vitamin B6 nmol/L | 99.78 | 57.19 | 51 | 100.69 | 69.89 | 51 | 137.29 | 148.21 | 49 | 320.18 | 155.82 | 49 |
| C-Reactive Protein mg/dL | 0.24 | 0.45 | 45 | 0.33 | 0.63 | 45 | 0.17 | 0.15 | 20 | 0.28 | 0.67 | 20 |
| homocysteine μmol/L | 9.95 | 10.24 | 54 | 9.28 | 8.43 | 54 | 8.90 | 2.54 | 53 | 8.13 | 2.28 | 53 |
| CP450 enzyme induction | 7.85 | 1.15 | 49 | 8.61 | 1.57 | 30 | 7.92 | 1.17 | 52 | 8.61 | 1.67 | 24 |
| ATP (oxygen consumption) | 0.99 | 0.19 | 54 | 1.14 | 0.19 | 30 | 0.98 | 0.18 | 52 | 1.15 | 0.15 | 30 |
| Urinary bile acids | 1.17 | 0.11 | 54 | 1.14 | 0.27 | 37 | 1.20 | 0.15 | 52 | 1.17 | 0.12 | 42 |
| ORAC | 6471 | 1723 | 53 | 6945 | 1675 | 53 | 6480 | 1601 | 54 | 6983 | 1849 | 54 |
| Micronuclei (per 1000) | 56.46 | 21.3 | 26 | 53.03 | 30.74 | 26 | 63.33 | 24.89 | 25 | 45.50 | 24.09 | 25 |
| Urinary F2 isoprostanes | 795.30 | 1211.92 | 50 | 924.16 | 1744.13 | 50 | 824.52 | 930.31 | 50 | 1618.06 | 2630.19 | 50 |
| vitamin B12 pg/mL | 393.35 | 168.13 | 49 | 408.80 | 174.59 | 49 | 475.8 | 184.0 | 46 | 661.8 | 246.4 | 46 |

The results of the clinical study shown in Table 8 above and the corresponding FIGS. 1-6 confirm beneficial increases in plasma levels of at least vitamins B6, B12, and C, and folate in the Double X group, but no or minimal change in the placebo group. Beta carotene, which can be converted to Vitamin A in the body, and vitamin E, another antioxidant were also increased significantly in the Double X group, but not the placebo group.

In relation to risk factors, homocysteine was reduced to a large extent relative to baseline. In the Micronucleus Assay, which is a conventional test that measures DNA damage in dividing cells, there was a significant reduction in DNA damage in the subjects who had consumed Double X for six weeks, but no significant change in the subjects that consumed placebo.

This controlled clinical study thus confirmed that the supplement of the present invention provides functional benefits, at least by lowered homocysteine levels and protected DNA, in healthy human subjects.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The invention claimed is:

1. A method for treating free radical DNA damage in a human, comprising;
   administering to the human a dietary supplement comprising a fruit ingredient, a vegetable ingredient and an herbal ingredient, the fruit ingredient being pomegranate, present in a dosage range of about 5 to about 500 mg/day, and citrus bioflavonoids, present in a dosage range of about 25 to about 1000 mg/day, the vegetable ingredient being at least one of asparagus, present in a dosage range of about 25 to about 1000 mg/day, lutein esters, present in a dosage range of about 0.1 to about 100 mg/day, lycopene, present in a dosage range of about 0.1 to about 100 mg/day, and watercress, present in a dosage range of about 5 to about 500 mg/day, and the herbal ingredient being at least one of basil, present in a dosage range of about 25 to about 1000 mg/day, oregano, present in a dosage range of about 25 to about 1000 mg/day, and rosemary, present in a dosage range of about 25 to about 1000 mg/day.

2. The method of claim 1 wherein the dietary supplement further comprises alfalfa, *brassica*, and kale.

3. The method of claim 1 wherein the dietary supplement further comprises sage and parsley.

4. The method of claim 1 wherein the dietary supplement further comprises at least one of vitamin A, vitamin C, vitamin D, vitamin E, niacin, vitamin $B_6$, vitamin $B_{12}$, folic acid, biotin, and pantothenic acid.

5. The method of claim 1 wherein the dietary supplement further comprises at least one of calcium, magnesium, iodine, potassium, copper, zinc, phosphorus, manganese, chromium, selenium, and molybdenum.

6. The method of claim 1 wherein the citrus bioflavonoids are in concentrate form and include naringen, hesperidin and narirutin.

7. A method for treating the occurrence of risk factors associated with disease states, comprising;
   administering to a human a dietary supplement comprising a fruit ingredient, a vegetable ingredient and an herbal ingredient, the fruit ingredient being pomegranate and citrus bioflavonoids, the vegetable ingredient being asparagus, lutein, lycopene and watercress, the herbal ingredient being basil, oregano and rosemary, wherein the fruit ingredient, the vegetable ingredient and the herbal ingredient are present in a ratio of 3.5:1:1;
   reducing free radical levels in the human with the dietary supplement; and
   reducing free radical related DNA damage in the human with the dietary supplement.

8. The method of claim 1 wherein the dietary supplement further comprises alfalfa, *brassica*, kale, sage and parsley.

* * * * *

UNITED STATES PATENT AND TRADEMARK OFFICE
CERTIFICATE OF CORRECTION

PATENT NO.        : 7,438,936 B2                                        Page 1 of 1
APPLICATION NO. : 11/363119
DATED             : October 21, 2008
INVENTOR(S)       : Huang et al.

It is certified that error appears in the above-identified patent and that said Letters Patent is hereby corrected as shown below:

Column 13, Line 12-Column 14, Line 11, Claim 7:
Cancel the text beginning with "7. A method for treating" to and ending "dietary supplement.", and insert the following claim --7. The method according to claim 1, wherein the fruit ingredient, the vegetable ingredient and the herbal ingredient are present in a ratio of 3.5:1:1.--

Signed and Sealed this

Seventh Day of April, 2009

JOHN DOLL
*Acting Director of the United States Patent and Trademark Office*